(12) United States Patent
Beck

(10) Patent No.: US 9,681,999 B2
(45) Date of Patent: Jun. 20, 2017

(54) MALE GARMENT

(75) Inventor: Jeffrey L. Beck, Centerfield, UT (US)

(73) Assignee: Paradigm Research LLC, Gunnison, UT (US)

( * ) Notice: Subject to any disclaimer, the term of this patent is extended or adjusted under 35 U.S.C. 154(b) by 70 days.

(21) Appl. No.: 13/468,568

(22) Filed: May 10, 2012

(65) Prior Publication Data

US 2013/0304014 A1 Nov. 14, 2013

(51) Int. Cl.
*A61F 13/15* (2006.01)
*A61F 13/74* (2006.01)
*A61F 13/471* (2006.01)

(52) U.S. Cl.
CPC ............ *A61F 13/74* (2013.01); *A61F 13/471* (2013.01)

(58) Field of Classification Search
CPC .... A61F 5/453; A61F 13/471; A61F 13/4915; A61F 5/4408; A61F 13/74; A61F 13/451
USPC ......................................................... 604/349
See application file for complete search history.

(56) References Cited

U.S. PATENT DOCUMENTS

| | | | |
|---|---|---|---|
| 1,490,793 A * | 4/1924 | Ajamian et al. | 604/350 |
| 2,310,505 A * | 2/1943 | Blackburn et al. | 604/350 |
| 2,445,220 A | 7/1948 | Isaacson | |
| 2,864,369 A | 12/1958 | Morrow | |
| 3,489,150 A * | 1/1970 | Glaude | A61F 5/453 604/353 |
| 3,550,590 A * | 12/1970 | Keilman | 602/73 |
| 4,197,849 A | 4/1980 | Bostick | |
| 4,668,229 A | 5/1987 | Fago et al. | |
| 4,790,834 A * | 12/1988 | Austin | 604/349 |
| 5,275,592 A * | 1/1994 | Grizzaffi | A61F 5/4401 2/403 |
| 5,524,298 A | 6/1996 | Plunkett | |
| 5,547,466 A | 8/1996 | McRoberts et al. | |
| 5,807,299 A | 9/1998 | McRoberts et al. | |
| 6,059,762 A * | 5/2000 | Boyer | A61F 13/471 604/349 |
| 6,113,582 A * | 9/2000 | Dwork | 604/349 |
| 6,132,412 A | 10/2000 | Jones | |
| 6,197,011 B1 | 3/2001 | Freitas et al. | |
| 6,419,665 B1 | 7/2002 | Cohen | |
| 6,443,930 B1 | 9/2002 | Silverstein | |
| 6,580,011 B1 | 6/2003 | Jennings-Spring | |
| 6,635,038 B2 | 10/2003 | Scovel | |

(Continued)

FOREIGN PATENT DOCUMENTS

JP 2002/306525 10/2002
KR 2010/0089964 8/2010

OTHER PUBLICATIONS

PCT/US2013/039870; filed May 7, 2013; Paradigm Research LLC; international search report dated Sep. 17, 2013.

*Primary Examiner* — Bradley Philips
(74) *Attorney, Agent, or Firm* — Thorpe North & Western LLP

(57) ABSTRACT

A garment for absorbing fluid discharge in a male subject includes an open-topped pouch to receive the penis of the subject and an absorbent material lining at least a portion of the pouch. A strap attached to an upper edge of the front portion of the pouch is designed to encircle the waist of the subject and secure the pouch. The pouch is free to move with the penis through a wide range of positions. A system for absorbing fluid discharge in a male subject can include the garment and an absorbent pad that can be inserted into the pouch.

20 Claims, 3 Drawing Sheets

(56) References Cited

U.S. PATENT DOCUMENTS

| | | |
|---|---|---|
| D491,264 S | 6/2004 | Dorn |
| 8,425,482 B2 * | 4/2013 | Khoubnazar ............ 604/385.09 |
| 8,568,376 B2 * | 10/2013 | Delattre et al. .......... 604/385.01 |
| 2002/0007160 A1 | 1/2002 | Miskie |
| 2003/0149409 A1 | 8/2003 | Lin |
| 2004/0106909 A1 | 6/2004 | Browning |
| 2009/0281510 A1 * | 11/2009 | Fisher ........................... 604/349 |
| 2011/0077610 A1 | 3/2011 | Kikumoto et al. |

* cited by examiner

MALE GARMENT

BACKGROUND

Incontinence in men, particularly urinary incontinence, can arise from a number of causes, and its effects can exhibit a wide range of severity and duration: from mild to severe, and from temporary to effectively permanent. Urine is made by the kidneys and stored in the urinary bladder. The path for the exit of urine and other products of the genitourinary system is provided by the urethra, which leads from the bladder through the prostate and penis to the outside of the body. The urinary sphincter, a ring of muscle surrounding the proximal part of the urethra, provides the principal proximate mechanism of control of flow through the urethra. With respect to continent urinary function, during filling of the bladder, nerve signals instruct the sphincter to stay squeezed shut and the bladder to relax. The nerves and muscles work together to prevent urine from leaking out of the body. Any condition or surgical intervention that disrupts this neuromuscular control can result in the inability to control the timing of bladder emptying, resulting in staining of clothing, attendant discomfort and embarrassment. In men, incontinence is often related to prostate problems or treatments. For example, partial or total removal of the prostate often results in a degree of stress incontinence or even functional incontinence. Other conditions can contribute to occasional or frequent episodes of incontinence, including kidney disease, overactive bladder, bladder infection, diabetes insipidus, alcohol use, as well as side effects of certain drugs.

While some causes of incontinence are addressable by treatment, others are not. In either case, the sufferer must deal with the unwelcome consequences of episodes of incontinence until the condition is relieved. Accordingly, potential benefit can come from devices and methods that prevent discharged fluid from staining clothes while providing comfort and ease of use.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1A:
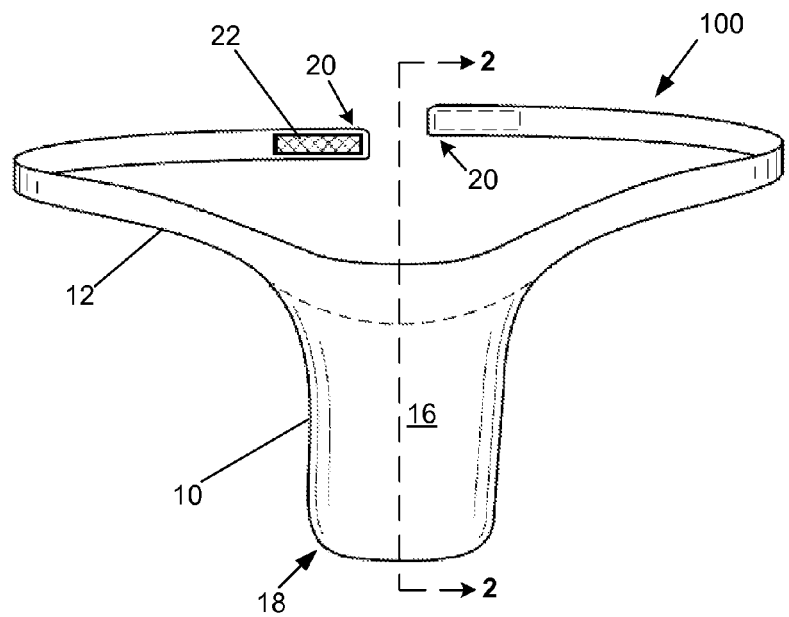
FIG. 1A is a front view of a garment in accordance with an embodiment of the present disclosure.

Reference will now be made to exemplary embodiments illustrated herein, and specific language will be used to describe the same. It will nevertheless be understood that no limitation of the scope of the invention is thereby intended.

DETAILED DESCRIPTION

In describing embodiments of the present disclosure, the following terminology will be used.

The singular forms "a," "an," and "the" include plural referents unless the context clearly dictates otherwise. Thus, for example, reference to a "fastener" includes reference to one or more of such fasteners.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a stated numerical range of "50-250 centimeters" should be interpreted to include not only the explicitly recited values of about 50 centimeters and 250 centimeters, but also include individual values and sub-ranges within the indicated range. Thus, included in this numerical range are individual values such as 60, 70, and 80 centimeters, and sub-ranges such as from 50-100 centimeters, from 100-200, and from 100-250 centimeters, etc. This same principle applies to ranges reciting only one numerical value and should apply regardless of the breadth of the range or the characteristics being described.

As used herein, the term "about" means that dimensions, sizes, parameters, shapes and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall expressly include "exactly," consistent with the discussion above regarding ranges and numerical data.

The term "incontinence" as used herein refers generally to any inability, whether acute or chronic, of a male subject to prevent discharge from the penis. A common form of incontinence involves involuntary discharge of urine, and this type of incontinence will often be used in the following description for purposes of explaining the aspects of the present technology. However, the present technology is considered to apply to any discharge that can occur from the penis (e.g. urine, semen, blood, or pus).

In an embodiment of the present technology, a garment for absorbing fluid discharge in a male subject comprises an open-topped pouch configured to receive therein the penis of the subject. The pouch is attached to a strap that encircles the waist of the subject and secures the pouch in place over the penis when the garment is worn. The attachment of the pouch to the strap is designed to allow the pouch to move freely and thereby assume nearly any position the penis assumes. The pouch includes an absorbent material for absorbing discharged fluid, e.g. urine.

Figure 1B:
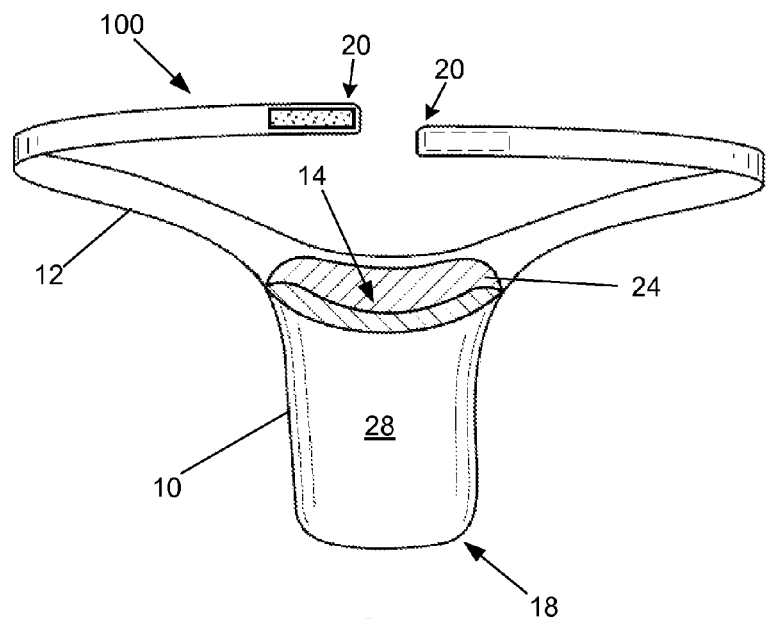
FIG. 1B is a rear view of the garment shown in FIG. 1.

The principles underlying the present disclosure can be understood by reference to example embodiments. FIGS. 1A and 1B respectively show front and rear views of a garment 100 according to an embodiment of the disclosure. A pouch 10 for receiving the penis of the subject is attached to a strap 12 designed for encircling the waist of the subject. The pouch is open at the top, providing an opening 14 for insertion of the penis into the pouch. A subject can put on the garment by securing the strap around his waist and placing the penis into pouch. The insertion and putting on can be done in any sequence permitted by the subject's anatomy and the design of the strap. Accordingly, a method for absorbing discharge from the penis can include putting on a garment according to the embodiments described herein. The arrangement of the components of the garment is such that when the subject is wearing the garment, the strap around the subject's waist holds the pouch in place on the penis. In another aspect, the attachment of the pouch to the strap permits the pouch to move as the penis moves. For example, such movements can result when the subject experiences an erection, or when the subject walks or runs, and also from changes in posture (e.g. sitting up, laying down, rolling over, and bending).

In one embodiment, the strap can be attached to or be continuous with an upper edge of the pouch. For example, as shown in FIG. 1B, the strap 12 can be of one piece with the front portion 16 of the pouch 10, so that the front portion of the pouch hangs directly from the strap. In a specific embodiment, the attachment of the strap to an upper edge of the pouch can be the sole point at which the pouch is attached to any other part of the garment 100. According to the embodiment, a distal end 18 of the pouch has no attachment to the rest of the garment, so that the pouch is therefore free to assume a similar range of angles relative to the subject's body as the penis does. In one aspect, the attachment is structured so that the pouch can rotate about the strap over at least one full revolution when the garment is not being worn. When the garment is in place on the subject, the movement of the pouch is limited only by the subject's anatomy. In a particular aspect, the pouch is configured to move over a range of at least about 200°. In a more specific aspect, the pouch is configured to move over a range of at least about 180°. In a still more specific aspect, the pouch is configured to move over a range of at least about 150°.

For example as shown in FIGS. 1A and 1B, the pouch 10 and strap 12 can be made of one continuous piece of material, where the material is sufficiently flexible to allow a range of movement such as indicated above. In alternative embodiments, the pouch and strap can be separate pieces, and the flexibility can be provided by attaching the respective pieces to each other via a flexible or articulated joint, such as a hinge, interlocking loops or rings, and the like.

As shown in FIGS. 1A and 1B, in one embodiment, the strap 12 itself can comprise a strip of material having two free ends 20 that can be engaged with one another in securing the strap around the waist. In one aspect, the free ends can be configured to be engaged by tying. In another aspect, at least one of the free ends can include a fastener 22 configured to fasten to the other free end or another part of the garment, and so hold the garment in place. Suitable fasteners include snaps, clasps, buttons, buckles, hook-and-loop fasteners such as Velcro®, and the like. In another embodiment, the strap can comprise a single continuous loop of material. In this case, the garment can be pulled on or off over the feet and legs like other undergarments or pants. In a more particular example, putting the garment on or taking the garment off, and achieving a secure fit on the body can be facilitated by inclusion of one or more elastic portions in the strap.

The garment of the present invention is contemplated for use as foundational garment, i.e. to be worn in place of or underneath other clothing such as underwear and pants. Accordingly, the garment can be made from any material suitable for use in undergarments and therefore that can be comfortably worn next to the skin. In a particular example, the material can be one that provides breathability and promotes wicking or evaporation of moisture from the underlying skin. Suitable materials include but are not limited to natural fabrics such as cotton, and synthetic fabrics comprising polyester or nylon. Another aspect of the garment can be preventing moisture from fully penetrating the garment and possibly contacting overlying clothing. Accordingly the garment can also include an outer layer designed to retain moisture within the material of the garment.

Figure 2:
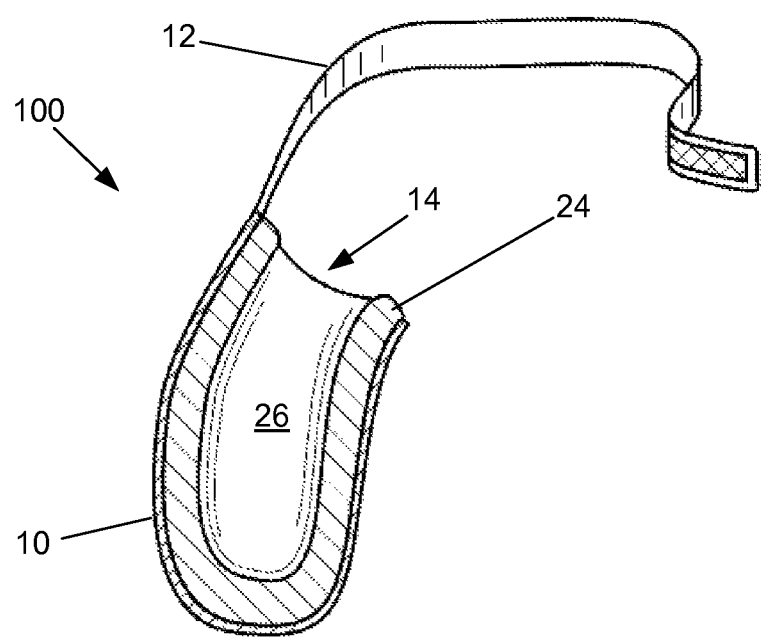
FIG. 2 is a cross-sectional view of the garment of FIGS. 1A and 1B, taken along line 2-2 in FIG. 1A.

The garment of the present invention can further include an absorbent material. The absorbent material can be situated to absorb any liquid discharge (e.g. an involuntary discharge of urine resulting from urinary incontinence). FIGS. 1B and 2 show an example of placement of absorbent material 24 situated in the pouch 10 of a garment 100 in accordance with the present technology. The absorbent material can comprise any material that is capable of readily absorbing liquid, including but not limited to cotton, cellulose, polyester, polyolefin, and the like. The absorbent material lines at least a portion of the pouch so as to effectively absorb liquid discharged from the penis of the subject. In one aspect, the absorbent material is arranged in the pouch so that discharged liquid makes contact with the material almost immediately after the liquid exits the penis. In a specific embodiment, the absorbent material is arranged to substantially surround the penis when the pouch is in place on the penis.

The absorbent material can be provided in any amount and in any form suitable for lining the pouch, including but not limited to woven cloth, wadding, absorbent foam, or gauze. In a particular aspect, the garment includes enough absorbent material to absorb a significant volume of liquid, so as to be effective in keeping the subject and his clothing dry after multiple small discharge events or at least one large accidental discharge. In an embodiment, the amount of absorbent material included is sufficient to absorb up to about 1.0 of liquid. In other embodiments, in accordance with the present disclosure, the amount of absorbent material is capable of absorbing up to about 0.8 of liquid, or up to about 0.6, or up to about 0.4, or up to about 0.2. The absorbent material can be arranged in two or more layers for added thickness, absorbency, or comfort. The layers can comprise multiple layers of a given material, or alternatively can comprise at least two different materials. In a particular embodiment, the absorbent material forms an absorbent pad that is shaped to line the pouch.

According to an embodiment, the absorbent material can be integrated into the structure of the pouch. FIG. 2 illustrates one example, in which the absorbent material 24 forms an interior lining in the pouch 10. In this design, the absorbent material defines a space 26 in which the penis is situated when the garment 100 is being worn. In another example, the absorbent material can be situated between two layers of other material to form the pouch. In more particular example, a single-use garment in accordance with the present technology includes this arrangement. A subject can put on the garment for a period of time to absorb any involuntary discharges, thereby keeping his other clothing dry. After a time, or once the absorbent material has reached its capacity in absorbed fluid, the garment can be removed and disposed of. In another example, a garment is made from a washable material and can further include a washable absorbent material integrated into the pouch. After use, this garment can be removed, washed, and then re-used.

In another embodiment, the absorbent material is removable and replaceable. In one example, the absorbent material (e.g. provided as an absorbent pad) can be inserted into the pouch before use. Once inserted, the absorbent material defines a space in which the penis is situated when the garment is being worn. As described above, the absorbent material can be shaped so as to substantially surround the penis. After use, the absorbent material is then removed and replaced. In one aspect, the absorbent material is disposable. In an alternate aspect, the absorbent material can constitute a washable insert that can be removed for washing and replaced between uses. In an embodiment, an insert comprising absorbent material can include features for removably securing the insert inside the pouch, such as one or more adhesive patches, pins, clips, hooks, or other suitable securing means.

In a particular embodiment, the pouch itself is evertible independent of the rest of the garment. Evertibility generally can facilitate a placement of things within the pouch to serve particular functions and uses of the garment. In one aspect, everting the pouch can facilitate placement and removal of absorbent material. For example, placement of an absorbent pad having an adhesive patch is aided by everting the pouch. That is, when the pouch is everted, the pad can be readily oriented to occupy a particular position in the pouch, and then the adhesive patch can be engaged to secure the pad. Once placement is achieved, the pouch can be reverted for use (e.g. insertion of the penis).

Figure 3:
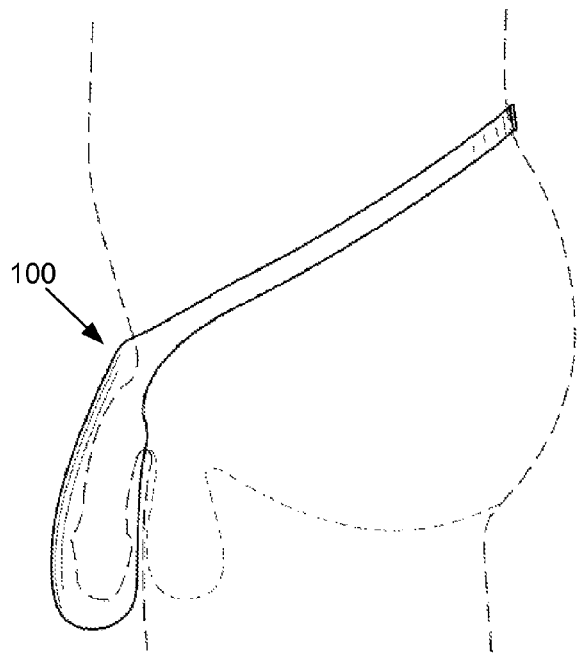
FIG. 3 is a side view of a garment in accordance with an embodiment of the present disclosure, shown superimposed on the anatomy of a male subject (dashed lines)

The pouch can include particular features that provide for effective placement on the penis and that can also enhance comfort and wearability. FIG. 3 shows an example of how a garment 100 according to the present technology can be situated on the anatomy (indicated by dashed lines) of a subject wearing the garment. As shown in FIGS. 1A, through 3 the pouch 10 is configured to hold only the penis of the subject while excluding the testicles. In this configuration, the rear portion 28 of the pouch 10 is situated between the penis and the scrotum. This design enhances the ability of the pouch to move freely with changes in the position of the penis. Another aspect of this configuration is that the rear portion of the pouch can act as a cushion between the penis and the scrotum, enhancing the comfort of the wearer. In accordance with the present technology, the garment can be designed to accommodate the male anatomy so as to allow such positioning. In typical human male anatomy, the scrotal raphe joins the penile raphe at a point on the penis that results in the ventral aspect of the penis being somewhat shorter than the dorsal aspect. This anatomical feature can limit the extent to which the penis can be inserted into a pouch having a conventional opening. In the present embodiment, however, the upper edge of the pouch is shaped so that substantially the entire length the penis can be inserted therein. In a particular example, as shown in FIG. 2, the upper edge of the pouch 10 is contoured so that the pouch has a lowered profile in the rear as compared to the front. As a result of this shape, the raphes do not present a barrier to full insertion of the penis into the pouch.

The cushioning effect of the rear portion of the pouch between the penis and scrotum can be enhanced by including thicker material or padding in that portion of the pouch. In one aspect, padding can be provided at least in part by the absorbent material. For example, the absorbent material can be positioned in the pouch so that at least some of the absorbent material is situated between the penis and scrotum when the garment is in place on the penis. In a specific embodiment, a length of absorbent material can overlap the upper edge of the pouch, and more specifically can overlap the rear portion of the upper edge, to provide cushion between the penis and the upper edge of the pouch.

Figure 4:
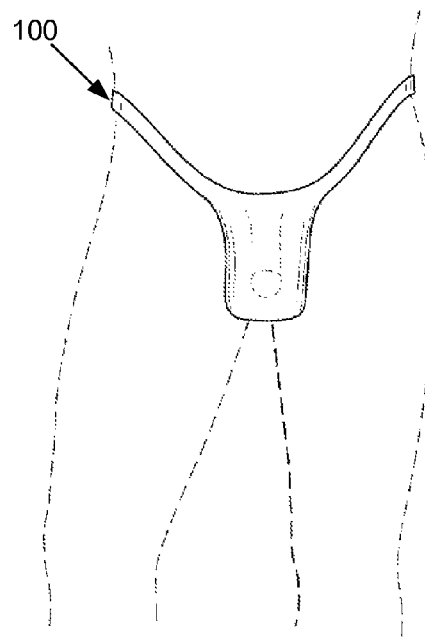
FIG. 4 is a front view of a garment in accordance with an embodiment of the present disclosure, shown superimposed on the anatomy of a male subject (dashed lines).

The strap of the present garment is configured to secure the pouch in place at least in part by encircling the waist of the subject. In a further aspect, the strap includes features or properties that enhance security and comfort when the garment is being worn. In one embodiment, the strap includes one or more features that provide a suitable fit on subjects having different waist sizes. In a specific example, the strap includes one or more elastic portions. In another example, the strap includes one or more buckles. In another aspect, the strap is configured to assume a particular position on the subject's body when the garment is worn. The positioning of the strap contributes to the distribution of any weight and pressures associated with the garment, which can affect the level of comfort experienced by the subject. This is particularly the case with regard to the pelvic bones, some of which include prominences where there is little intervening tissue between the bone and the overlying skin. The skin overlying these features is therefore subject to pinching and chafing due to compression by snug-fitting overlying garments. In a specific example, the strap is configured to align with a feature of the subject's pelvis. One aspect of such alignment is that the strap can interact with the pelvis in a way that supports the garment while avoiding the creation of pressure points that can cause discomfort. In a more specific embodiment, the strap is configured to substantially align with the iliac crest of the pelvis. FIG. 4 shows a garment 100 in place on a subject (indicated by dashed lines) and exhibiting such an alignment.

A plurality of components such as those described above can be combined to provide a system for absorbing liquid discharge in a male subject. In one embodiment of the present technology, a system includes a garment comprising an open-topped pouch with a strap attached to an upper edge of the pouch. The strap and pouch can include any of the features and functionalities discussed above. In a particular embodiment, the strap is configured to encircle the waist of the subject and secure the pouch so that the pouch is free to move with the penis through a range of at least about 150°. The system further includes an absorbent pad that is configured for insertion into the pouch. The absorbent pad can include any of the features discussed above with regard to material, structure, and other properties. It is contemplated that the absorbent pad comprise a separate insertable component, and therefore can also be removable and can be replaced for a subsequent use of the garment. In a particular embodiment, the absorbent pad is disposable. A system according to this embodiment can include multiple disposable pads to extend service life. In another embodiment, the system includes a washable absorbent pad.

A method of addressing the effects of liquid discharge in a male subject can comprise putting a garment in accordance with the present invention on the subject. The method includes the steps of inserting the subject's penis into the open-topped pouch and securing the strap around the subject's waist. As noted above, insertion of the penis and securing the garment can be done in any sequence permitted by the subject's anatomy and the design of the strap. For example, when a continuous-loop waist strap is used, the garment can be put on and adjusted to a suitable position, and then the penis can be inserted. Alternatively, when the strap includes two ends that can be tied or fastened, the penis can be inserted into the pouch before securing the strap around the waist. Further, the design of the pouch allows for removal and replacement of the absorbent material (in embodiments in which said material is removable) without the need to remove the garment. That is, because the distal end of the pouch is unattached, the pouch can be pulled off of and placed back onto the penis while the subject is still wearing the garment. Therefore, access to the interior of the pouch and any other adjustments can be accomplished with minimal disturbance of overlying clothing.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A garment for absorbing fluid discharge in a male subject, comprising:
   an open-topped pouch to receive the penis of the subject, wherein the pouch is configured to hold only the penis while being insufficient to hold both the penis and the scrotum of the subject such that the scrotum is excluded from the pouch;
   an absorbent material lining at least a portion of the pouch; and
   a waist strap attached to an upper edge of a front portion of the pouch at an attachment location configured to abut a point of attachment of the penis to the male subject, and wherein the waist strap is configured to encircle the waist of the subject and secure the pouch so that the pouch is free to move with the penis through a range of at least about 150° independent of the scrotum, and wherein the waist strap is configured to substantially align with the iliac crest.

2. The garment of claim 1, wherein the upper edge of the front portion of the pouch is positioned higher than an upper edge of a rear portion of the pouch.

3. The garment of claim 1, wherein the absorbent material is situated so as to substantially surround the penis when the pouch is in place.

4. The garment of claim 1, wherein the absorbent material is configured to absorb up to about 1.0 mL of liquid.

5. The garment of claim 1, wherein the absorbent material is removable.

6. The garment of claim 1, wherein the waist strap and the front portion of the pouch are one continuous piece of material.

7. The garment of claim 1, wherein the waist strap includes an elastic portion.

8. The garment of claim 1, wherein the waist strap includes two free ends that can be tied together to secure the waist strap around the waist.

9. The garment of claim 1, wherein the waist strap comprises a continuous loop.

10. The garment of claim 1, wherein the waist strap includes a fastener selected from the group consisting of snaps, buttons, hook-and-loop fasteners, clasps, and buckles.

11. The garment of claim 1, wherein the pouch is configured so that a rear portion of the pouch is interposed between the penis and the scrotum of the subject when the pouch is in place.

12. The garment of claim 1, wherein the absorbent material is situated so as to substantially surround only the penis when the pouch is in place.

13. The garment of claim 1, wherein the pouch is free to move with the penis through a range of at least about 180° independent of the scrotum.

14. The garment of claim 13, wherein the pouch is free to move with the penis through a range of at least about 200° independent of the scrotum.

15. A system for absorbing fluid discharge in a male subject, comprising:
   a garment comprising an open-topped pouch to receive the penis of the subject, wherein the pouch is configured to hold only the penis while being insufficient to hold both the penis and the scrotum of the subject such that the scrotum is excluded from the pouch, the pouch having an upper edge attached to a waist strap at an attachment location configured to abut a point of attachment of the penis to the male subject, and wherein the waist strap is also configured to encircle the waist of the subject and secure the pouch so that the pouch is free to move with the penis through a range of at least about 150° independent from the scrotum, and wherein the waist strap is configured to substantially align with the iliac crest; and
   an absorbent pad configured for insertion into the pouch.

16. The system of claim 15, wherein the absorbent pad is configured to line the pouch so as to substantially surround the penis when the pouch is in place.

17. The system of claim 15, wherein the upper edge of the pouch has a front portion and a rear portion and wherein the front portion is positioned higher than the rear portion.

18. The system of claim 15, wherein the absorbent pad is disposable.

19. The system of claim 15, wherein the waist strap includes fasteners selected from the group consisting of snaps, buttons, hook-and-loop fasteners, clasps, and buckles.

20. The system of claim 15, wherein the pouch is configured so that a rear portion of the pouch is interposed between the penis and the scrotum of the subject when the pouch is in place.

* * * * *